United States Patent [19]

Bostater, Jr.

[11] Patent Number: 5,751,424
[45] Date of Patent: May 12, 1998

[54] SCALABLE NON-CONTACT OPTICAL BACKSCATTER INSERTION PROBE

[75] Inventor: Charles R. Bostater, Jr., Indian Harbour Beach, Fla.

[73] Assignee: KB Science, Beaufort, S.C.

[21] Appl. No.: 743,789

[22] Filed: Nov. 5, 1996

[51] Int. Cl.[6] .................... G01N 21/00; G01N 21/55
[52] U.S. Cl. .................... 356/342; 356/439; 356/440; 356/442; 356/445
[58] Field of Search .................... 356/335–336, 356/338, 342, 442, 339–341, 436–440; 250/222.24, 222.25

[56] References Cited

U.S. PATENT DOCUMENTS

| | | |
|---|---|---|
| 3,826,557 | 7/1974 | Lobb et al. |
| 3,990,795 | 11/1976 | Parker |
| 4,006,988 | 2/1977 | Tamm |
| 4,022,534 | 5/1977 | Kishner .................... 356/446 |
| 4,226,540 | 10/1980 | Barten et al. |
| 4,272,156 | 6/1981 | Ishibashi et al. .................... 385/117 |
| 4,707,134 | 11/1987 | McLachlan et al. .................... 356/342 |
| 4,774,417 | 9/1988 | Houpt |
| 4,816,670 | 3/1989 | Kitamura et al. |
| 4,983,040 | 1/1991 | Chu et al. |
| 5,208,465 | 5/1993 | Jacobson |
| 5,231,378 | 7/1993 | Dennis et al. |
| 5,453,832 | 9/1995 | Joyce |
| 5,459,568 | 10/1995 | Yano et al. |
| 5,625,459 | 4/1997 | Driver .................... 356/446 |

*Primary Examiner*—David C. Nelms
*Assistant Examiner*—Jason D. Vierra-Eisenberg
*Attorney, Agent, or Firm*—Covington & Burling

[57] ABSTRACT

A non-contact optical backscatter insertion probe includes an outer chamber, an electromagnetic energy source positioned within the outer chamber for emitting photons towards a medium to be analyzed, and an inner chamber positioned within the outer chamber. The inner chamber has a reflective outer surface to prevent photons emitted by the electromagnetic energy source in the outer chamber from entering the inner chamber. The probe also includes a sensor positioned within the inner chamber for receiving backscattered photons from the medium. The inner chamber provides the backscattered photons emitted from the medium to the sensor. A processor receives and processes signals output by the sensor. Similarly, a method for measuring optical backscatter from a medium to be analyzed includes the steps of providing an electromagnetic energy source positioned within an outer chamber of an optical backscatter probe to emit photons towards a medium to be analyzed; providing a sensor positioned within an inner chamber of the optical backscatter probe to receive backscattered photons from the medium wherein the inner chamber provides the backscattered photons emitted from the medium to the sensor; and processing signals output by the sensor.

14 Claims, 4 Drawing Sheets

1

SCALABLE NON-CONTACT OPTICAL BACKSCATTER INSERTION PROBE

FIELD OF THE INVENTION

The present invention relates to a non-contact optical backscatter insertion probe for measuring backscattered light from a liquid, solid or gas medium. The measured backscattered light signal or spectral signature from a medium is analyzed to estimate the constituents or chemical composition of the medium. The probe is scalable in size for both large-scale and small-scale applications.

BACKGROUND OF THE INVENTION

There are numerous techniques for analyzing the chemical constituents of a liquid mixture, gas or solid medium by relating selected optical properties of a liquid or other medium to the constituents and their concentrations within the medium. Many of these techniques measure the reflectance, scattering, transmittance or attenuation of electromagnetic energy. Another technique is to measure backscattered electromagnetic energy (EME) from a medium in response to light falling on or entering the medium in a given direction. The measurements of spectral signatures of a medium are generally analyzed by application of algorithms, mathematical models and/or solutions of radiative transfer theory. The ability to measure the backscattered light directly enables scientists and application engineers to utilize this signal to estimate constituents of a medium more easily and accurately, as well as to improve understanding of radioactive transfer phenomena.

There are a number of known methods for measuring EME backscatter of a medium. A few of these methods are described in U.S. Pat. Nos. 3,990,795; 4,006,988; 4,226,540; 4,774,417; and 4,983,040. However, the known methods for measurement of EME backscattering do not enable measurement of the EME backscatter from a medium by using a probe of relatively simple design which is easy to construct, scalable for use in numerous applications, corrosion-resistant, measures EME backscattering substantially simultaneously (i.e., in near real time) to the emission of EME from a energy source into the medium, without surface reflectance effects in the case of liquid medium, and in which the sensor does not contact the medium.

SUMMARY OF THE INVENTION

In view of the above-described drawbacks to the known devices for measuring EME backscattering in a medium, the present invention relates to a scalable, non-contact, optical backscatter insertion probe for measuring backscattered EME from a liquid, solid or gas medium. According to the present invention, the medium to be measured is backlit such that the EME source does not touch the medium. Photons upwelling from the medium are backscattered into an optical chamber. A sensor is positioned at the top of the inner chamber and does not touch the medium. As a result of this novel structure, neither the EME source nor the sensor are in contact with the medium (e.g., a liquid) being studied and therefore are in no way affected or damaged by the medium.

A non-contact optical backscatter insertion probe according to the present invention includes an outer chamber, an EME source positioned within the outer chamber for emitting photons towards or into the medium to be analyzed, and an inner chamber positioned within the outer chamber. The inner chamber has a very high reflectance outer surface to maximize photons emitted by the EME source that enter the medium. The probe also includes a sensor positioned within the inner chamber. The inner surface of the inner chamber has extremely low or high reflectance for receiving backscattered photons from the medium. The use of a low or high reflectance coating allows for a broader range of applications. The inner chamber provides or channels the backscattered photons emitted from the medium to the sensor. A data link provides signals output by the sensor to a signal processor for processing the signals generated by the sensor. The sensor can be a single or multi-wavelength detector.

A method for measuring the optical backscatter or coefficient of backscatter from a medium to be analyzed according to the present invention includes the steps of (a) providing an EME source positioned within an outer chamber of an optical backscatter probe to emit photons towards a medium to be analyzed; (b) providing a sensor positioned within an inner chamber of the optical backscatter probe to receive backscattered photons from the medium wherein the inner chamber provides the backscattered photons emitted from the medium to the sensor; and (c) processing signals output by the sensor.

Thus, the present invention provides a probe of relatively simple design which is easy to construct, scalable for use in numerous applications, resistant to corrosive activity caused by exposure to the medium to be analyzed and the surrounding environment, and measures EME backscattering substantially simultaneously to the emission of light into the medium.

The foregoing and other features, aspects, and advantages of the present invention will become more apparent from the following detailed description when read in conjunction with the accompanying drawings.

DETAILED DESCRIPTION

The present invention will now be described with reference to the accompanying drawings.

Figure 1:
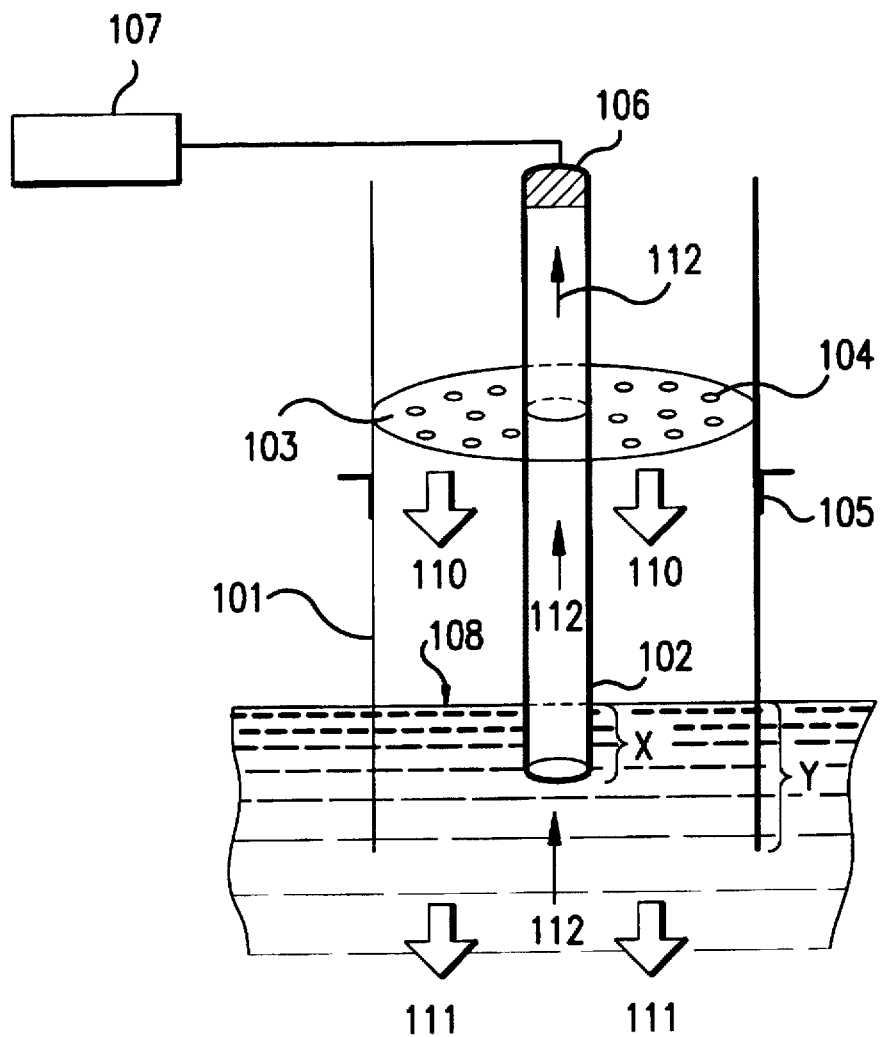
FIG. 1 provides an illustration of a scalable non-contact optical backscatter insertion probe according to the present invention.

FIG. 1 provides an illustration of a scalable non-contact optical backscatter insertion probe according to the present invention. As shown in FIG. 1, the probe comprises an outer optical chamber 101, an inner optical chamber 102, a scalable and movable light table 103 having a number of EME sources 104 positioned thereon, an optional mounting collar or bracket 105, a sensor 106, and a processor 107.

The outer optical chamber 101 may have a cylindrical shape as shown in FIG. 1 or other shapes as are suitable for the applications for which the probe is utilized. The outer optical chamber may be made of a metal such as aluminum, pvc-type plastic, a hardened fiber-resin, teflon type plastic, or other suitable materials. The outside wall of the chamber may be coated with an antifouling paint or other anti-corrosive material, or metal substrate. The inner wall of the chamber is coated with a high reflective coating.

The inner optical chamber 102 may have cylindrical shape as shown in Figure or other shapes as are suitable for the applications for which the probe is used. The inner optical chamber 102 may be made of a metal, plastic, fiber resin, or other suitable materials. The outer surface of the inner optical chamber is highly reflective to insure that photons (EME) emitted by the light source 104 do not enter the inner optical chamber directly, but instead enter the inner optical chamber only when backscattered from the medium to be analyzed. The inner surface of the inner optical chamber is coated for highly absorbing EME for most applications and may also be baffled to prevent side-scatter of photons off the walls of the inner chamber to insure that only direct backscattered photons (EME) reach the sensor 106. Alternatively, the inner surface of the inner optical chamber 102 may be a highly reflective surface, e.g., a diffuse reflector, to eliminate any polarization effects of the upwelled light which may adversely affect the sensor's measurement of backscattered EME. The coatings can be any special paint or coating made of an emulsified powder, such as barium sulfate or other dark substrate such as carbon black or a mixture coating with carbon black. The coating, whether high or low reflective, should have a nearly diffuse lambertion reflectance.

The diameter of the inner optical chamber 102 is usually determined by the field of view (FOV) of the sensor 106. Generally, for liquid measurement applications, the diameter of the inner chamber is equal to or on the same order of size as the FOV. The length of the outer optical chamber 101 is generally equal to or greater than the length of the inner optical chamber 102. For example, if the medium to be analyzed is a liquid, the inner optical chamber 102 is positioned below the surface of the liquid to eliminate surface reflectance such that only subsurface backscattered light is collected by the sensor. The outer optical chamber 101 is also inserted into the medium and extends beyond the depth of the inner optical chamber 102 as illustrated in FIG. 1. The ends of the chambers 101 or 102 may be secluded from the environment or medium by a clear plastic or lens type of fitting. In FIG. 1, X represents the depth of the inner optical chamber 102 below the surface of the medium 108 and Y represents the depth of the outer optical chamber 101 below the surface of the medium such that $X \leq Y$.

The preferred relative positioning of the inner and outer optical chambers when the medium is a solid or gas is generally equal to one another. However, if $X<Y$ for a solid, the surface reflectance or surface backscattering is included in the measured backscattered light by the probe. Thus, the lengths of the inner and outer chambers and the effective diameter of the inner and outer chambers are scalable in dimensions. However, the inner chamber diameter must be less than the outer chamber diameter.

The light table 103 is also scalable to fit the dimensions of the outer optical chamber 101 and the inner chamber 102. The light table 103 is also movable along and within the outer optical chamber 101 to adjust the distance between the EME sources 104 and the medium to be analyzed as desired. The light table 103 has one or more EME sources 104 positioned thereon. The EME source(s) 104 may be, for example, laser(s), LED(s) or broad band light (e.g., halogen quartz or tungsten) sources.

The sensor 106 may be a commercially available monochrometer, spectrograph, multi-wavelength linear diode array (LDA), charge coupled device (CCD) or charge induced device (CID) type sensor, any multi-wavelength spectral sensor, silicon diodes or similar light sensitive sensor. According to a preferred embodiment of the present invention, the sensor 106 is a multi-wavelength linear diode array sensor with high radiometric, spectral and temporal resolution mounted as a solid state camera head. For example, in a study of multiple wavelength excitation and emission spectroscopy, the sensor 106 may be an analog or digital camera, photo-multiplier tube (P.M.T.) or similar device, and the EME source 104 may be a laser, thus resolving fluorescence backscatter emission of the medium.

Data collected by the sensor 106 is provided to a remote processor via a hardwired or wireless data or signal link as are well-known in the art. The processor 107 receives data collected by the sensor 106 and processes the received data according to the particular analysis to be performed. For example, the data from the sensor may be analyzed by the processor 107 using optimal passive or active correlation spectroscopy techniques. The processor may also include one or more storage devices (not shown) for storing the received sensor data and the results of the data analysis.

A processor for use in the present invention may be, for example, an analog to digital converter integrated with a commercially available original equipment manufacturer (OEM) computer.

Notably, the scalable, non-contact optical backscatter insertion probe according to the present invention may also be used to measure reflectance and other optical characteristics of the medium as desired.

The operation of the non-contact optical backscatter probe shown in FIG. 1 is as follows. EME 110 is emitted by EME sources 104 on light table 103. The emitted EME enters the medium to be analyzed as represented by arrows 111. Some of the EME 111 in the medium is backscattered by the medium or constituents in the medium. A portion 112 of the backscattered EME is collected by the inner optical chamber 102 and directed to the sensor 106. The sensor 106 generates signals in response to the received EME 112 and provides these signals to processor 107 for processing.

The determination of chemical concentrations of constituents in a liquid medium using a non-contact optical backscatter insertion probe according to the present invention may be accomplished through the use of a multiple wavelength inversion methodology which is derived from radiative transfer theory, i.e., basic differential equations which describe the two-flow nature of EME within a liquid medium and the water-air interface. This analysis may combine a first, second or higher order derivative or inflection analysis of the optical signatures for optimal band detection followed by inversion techniques using solutions to differential equations which conduct an energy balance on the medium within a specified portion of the EM spectrum (e.g., a specified channel or waveband). The analysis technique may utilize solely derivative spectroscopy. Components of complex mixtures may also be determined through application of eigenvalue analysis of the optical signature of backscattered light. When a high degree of precision is required with chemicals with similar optical backscatter characteristics, optical clean up techniques can be used for signature analysis.

Figure 2:
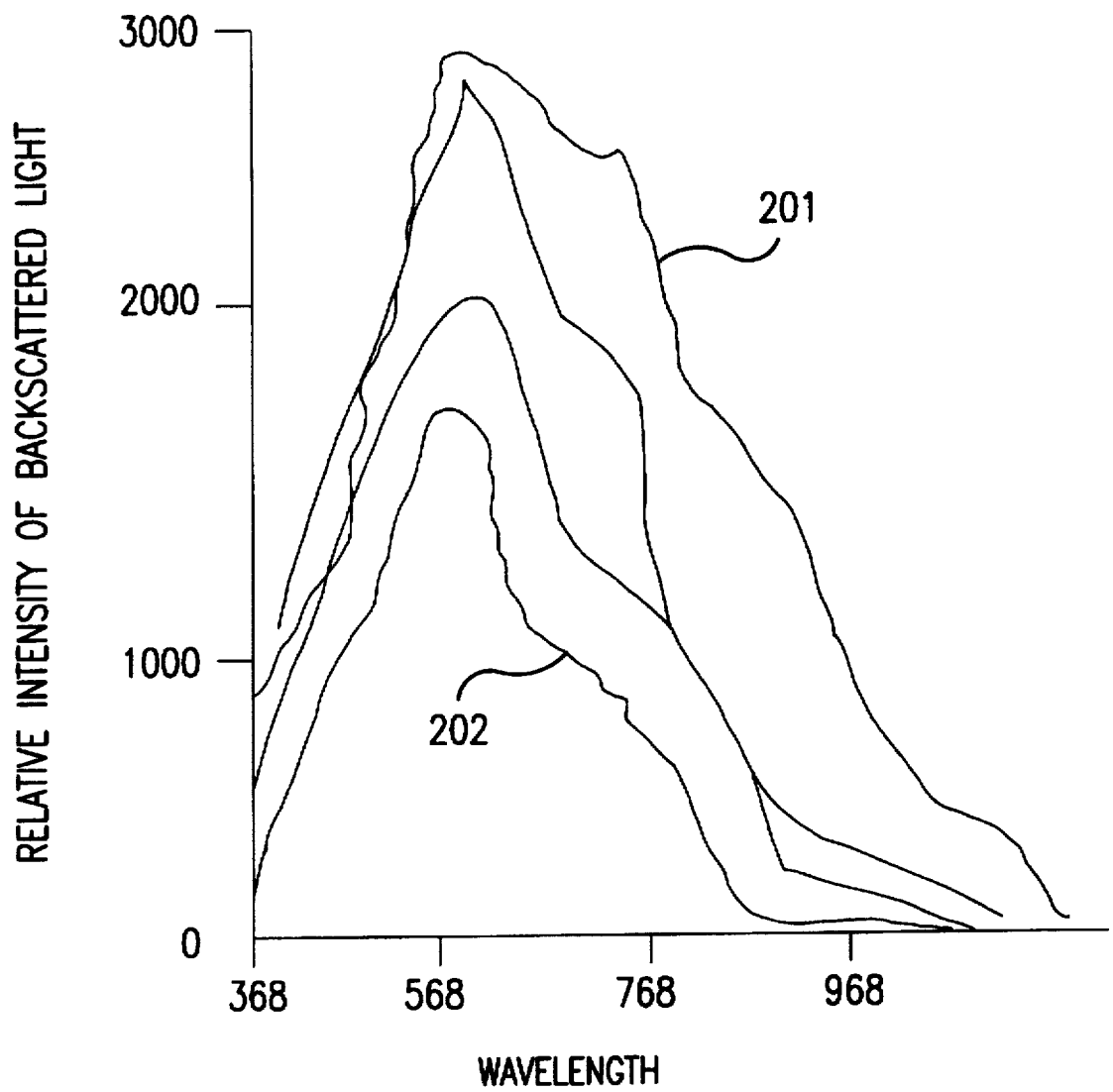
FIGS. 2, 3A, 3B, and 4 provide examples of the results of analyses of the data obtained by a probe according to the present invention as used to measure water having varying constituent concentrations.
Figure 3A:
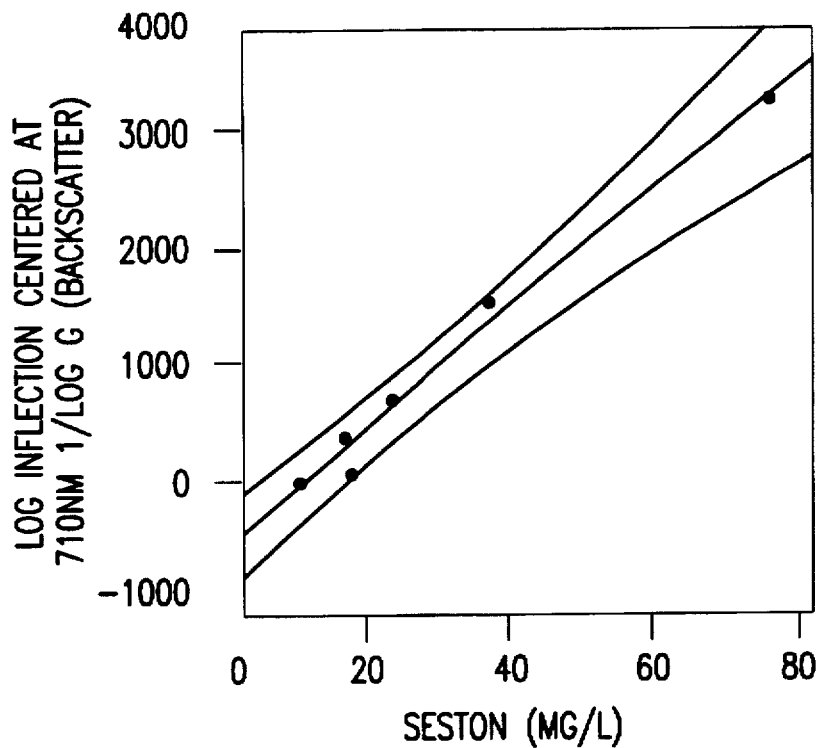
Figure 3B:
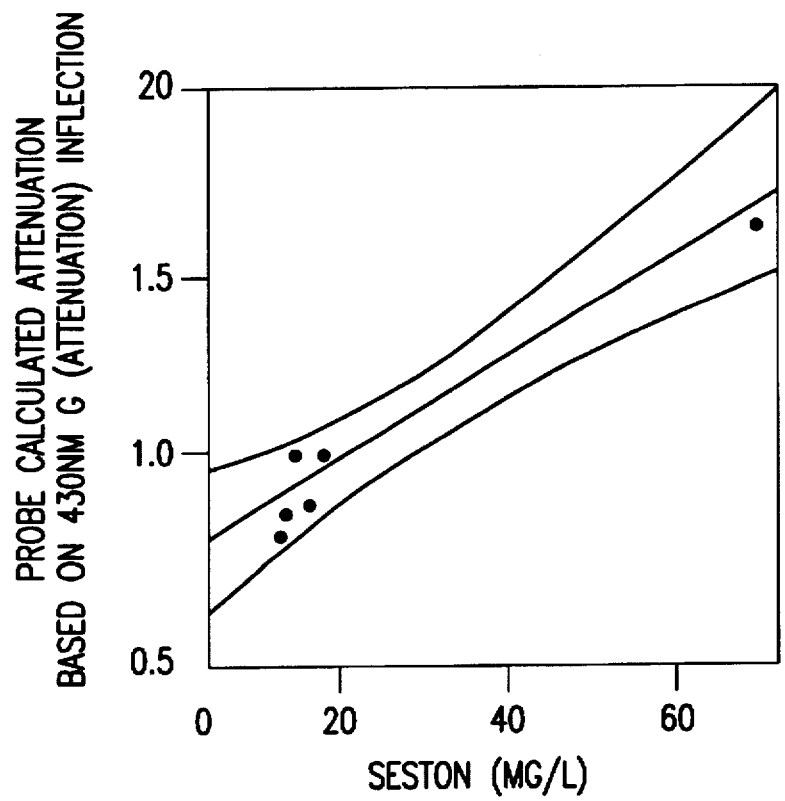
Figure 4:
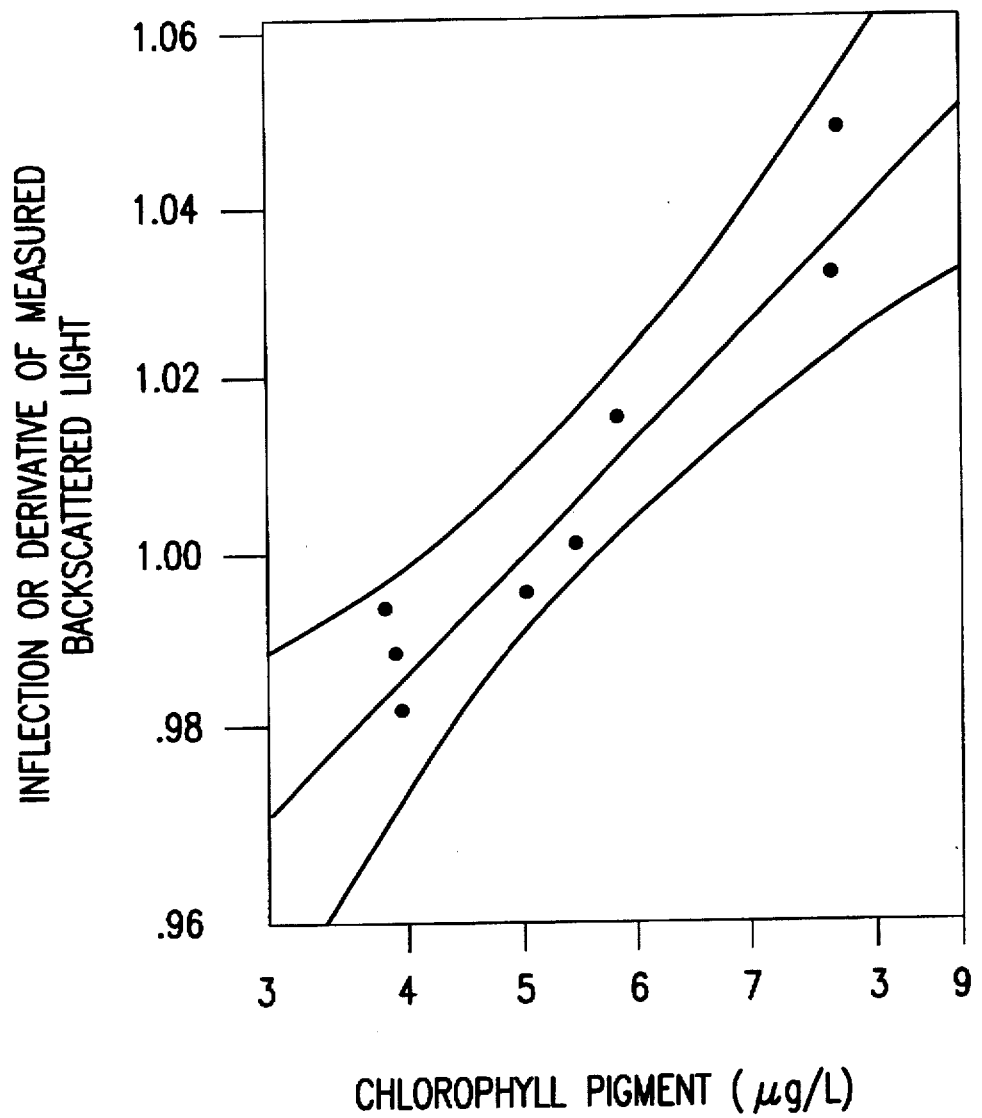

Examples of measured relationships between the measured backscattered EME spectrum and the chemical composition of a liquid medium are illustrated in FIGS. 2 through 4. These figures demonstrate the applicability of the probe to provide data sufficient to determine chemical or constituent concentrations in water ranging from clear water to highly turbid waters such as typical wastewater or industrial process streams or water.

FIG. 2 illustrates the variations in backscattered EME collected from different types of marine waters - from highly turbid fresh water (201) to cleaner, near-coastal waters (202). By calculating both the magnitude and wavelength shifts of the backscattered EME directly or normalized to the EME emitted into the water, the identity and concentration of substances in the water may be determined. The broader curves represent waters with more turbid characteristics.

FIGS. 3A and 3B illustrate the relationship between the concentration of total suspended matter (seston) in a complex water sample from an estuarine environment and a measure of the optical inflection (non-linear derivative estimator). Thus, the signatures of light intensity of subsurface backscattered light measured from the probe normalized to the EME impinging from the light table can be analyzed to predict the constituents in water as well as selection of the optimal wavelengths to use for detection or monitoring a medium.

FIG. 4 illustrates the relationship between the concentration of chlorophyll and a measure of the optical inflection (at a different location in the spectrum than shown in FIGS. 3A and 3B). This graph illustrates the technique of measuring subsurface backscattered light that can be used to measure pigments in a liquid medium using the sensor, processor, scalable probe, and analysis procedures described above.

The non-contact scalable optical backscatter insertion probe according to the present invention is suited to numerous commercial applications, such as measurement of concentration of various materials in water, such as wastewater, and process slurries. Given a specified waste or process stream, the probe according to the present invention may be custom designed (scaled) for the application. The probe may also be integrated into a processing plant's computer system to provide information on the contents of wastewater, process slurries and other media on a continual basis and to create a continuous record of the concentration of substances in the media.

According to other embodiments of the present invention, the scalable probe may also be made much smaller, e.g., on the order of size as a fiber optic cable (nominally≦0.1 cm) or the size of a test tube or similar optical cell. For example, living plant or animal tissue types can be assessed for composition and or texturally measured differences with the backscattered light dependent upon cellular level changes. The probe can also be used to measure liquid substrates or a gas placed in or flowing through a test tube or sample cell, with the probe being inserted into the top of the tube or cell. For example, the probe according to the present invention may be used for the analysis of bloods, pharmaceuticals, serums, chemical concentrates, gases, etc.

While the present invention has been particularly described with reference to the preferred embodiments, it should be readily apparent to those of ordinary skill in the art that changes and modifications in form and details may be made without departing from the spirit and scope of the invention. It is intended that the appended claims include such changes and modifications.

We claim:

1. A scalable optical backscatter probe, comprising:
   an outer optical chamber:
   an electromagnetic energy source positioned within said outer optical chamber for emitting photons towards a medium to be analyzed, wherein said photons emitted by said electromagnetic energy source are scattered within said outer optical chamber to enter said medium at a plurality of angles;
   an inner optical chamber having a reflective outer surface and an absorbing inner surface, said inner optical chamber collecting a portion of backscattered photons emitted from said medium;
   a sensor positioned within said inner optical chamber for receiving said backscattered photons collected by said inner optical chamber; and
   a link for providing signals output by said sensor to a processor for processing said signals.

2. An optical backscatter probe according to claim 1, wherein said medium is a liquid.

3. An optical backscatter probe according to claim 2, wherein said outer optical chamber and said inner optical chamber extend into said medium.

4. An optical backscatter probe according to claim 1, wherein said link is a hardwired link.

5. An optical backscatter probe according to claim 1, wherein said link is a wireless link.

6. An optical backscatter probe according to claim 1, wherein said electromagnetic energy source is positioned around said inner optical chamber.

7. An optical backscatter probe according to claim 1, wherein said medium is a gas.

8. An optical backscatter probe according to claim 1, wherein said medium is a solid.

9. A scalable optical backscatter insertion probe for measuring diffusely backscattered photon flux of a medium to be analyzed, comprising:
   an outer chamber having a first side wall, wherein said first side wall extends into said medium, said medium filling a bottom portion of said outer chamber;
   an electromagnetic energy source positioned within said outer chamber for emitting photons towards said medium, wherein said photons emitted by said electromagnetic energy source are scattered within said outer chamber to enter said medium at a plurality of angles;
   an inner chamber positioned within said outer chamber, said inner chamber having an absorbing inner surface and a reflective outer surface to prevent photons emitted by said electromagnetic energy source in said outer chamber from entering said inner chamber, said inner chamber having a second side wall, wherein said second side wall extends into said medium, said medium filling a bottom portion of said inner chamber;
   a sensor positioned within said inner chamber for receiving a portion of backscattered photons emitted from said medium, said inner chamber providing said portion of backscattered photons to said sensor; and
   a link for providing signals output by said sensor to a processor for processing said signals.

10. An optical backscatter probe according to claim 9, wherein said medium is a liquid.

11. An optical backscatter probe according to claim 10, wherein said outer chamber extends further into said medium than said inner chamber.

12. An optical backscatter probe according to claim 9, wherein said electromagnetic energy source in said outer chamber is positioned around said inner chamber.

13. An optical backscatter probe according to claim 9, wherein said medium is a gas.

14. A method of measuring backscattered electromagnetic energy emitted from a medium to be analyzed, comprising the steps of:
   providing an electromagnetic energy source positioned within an outer chamber of an optical backscatter probe to emit photons towards a medium to be analyzed, wherein said photons emitted by said electromagnetic energy source are scattered within said outer chamber to enter said medium at a plurality of angles;
   providing a sensor positioned within an inner chamber of said optical backscatter probe to receive a portion of backscattered photons emitted from said medium, said inner chamber providing said portion of backscattered photons emitted from said medium to said sensor; and
   processing signals output by said sensor upon receipt of said portion of backscattered photons.

* * * * *